United States Patent
Denesuk et al.

(10) Patent No.: US 6,178,922 B1
(45) Date of Patent: Jan. 30, 2001

(54) MASTICATION ARTICLE POSSESSING MICROBE-INHIBITING PROPERTIES

(75) Inventors: Matthew Denesuk; Eugenie V. Uhlmann, both of Tucson, AZ (US)

(73) Assignee: Seefar Technologies, Inc., Tucson, AZ (US)

(*) Notice: Under 35 U.S.C. 154(b), the term of this patent shall be extended for 0 days.

(21) Appl. No.: 09/250,072

(22) Filed: Feb. 12, 1999

Related U.S. Application Data

(63) Continuation-in-part of application No. 09/241,591, filed on Feb. 2, 1999, now abandoned, and a continuation-in-part of application No. 09/059,956, filed on Apr. 14, 1998, now abandoned.

(60) Provisional application No. 60/043,014, filed on Apr. 15, 1997.

(51) Int. Cl.$^7$ ............................................. A01K 29/00
(52) U.S. Cl. ................................................ 119/710
(58) Field of Search ...................... 119/709, 710, 119/711; 424/400, 52

(56) References Cited

U.S. PATENT DOCUMENTS

| | | | |
|---|---|---|---|
| 4,364,925 | * 12/1982 | Fisher | 119/710 |
| 4,419,372 | 12/1983 | Greene et al. | 119/710 |
| 4,557,219 | 12/1985 | Edwards | 119/710 |
| 4,674,444 | 6/1987 | Axelrod | 119/710 |
| 5,033,410 | * 7/1991 | Sigurdsson | 119/710 |
| 5,100,651 | * 3/1992 | Boyer | 424/52 |
| 5,114,704 | 5/1992 | Spanier et al. | 119/710 |
| 5,215,038 | 6/1993 | O'Rourke | 119/710 |
| 5,263,436 | 11/1993 | Axelrod | 119/710 |
| 5,310,541 | 5/1994 | Montgomery | 119/710 |
| 5,329,881 | 7/1994 | O'Rourke | 119/710 |
| 5,339,771 | 8/1994 | Axelrod | 119/710 |

(List continued on next page.)

OTHER PUBLICATIONS

Affidavit of Dennis Curley of Lazy Pet, Dated May 29, 1997, 2 Pages.
Ultra–Fresh Antimicrobials Brochure Undated, 1 Page.
Typical Ultra–Fresh* USES Brochure Undated, 1 Page.
Examples of Micro–Organisms That Ultra–Fresh* Products Inhibit Brochure Undated, 1 Page.
Examples of Antimicrobial Testing (Ultra–Fresh) Brochure Undated, 1 Page.
A Sample of Microbial Test Methods Available Brochure Undated, 1 Page.
Letter from Ron Tatar of Crain Industries, Inc. to Dennis Curley re: Anti–Microbial additive suppliers Undated, 1 Page.
Letter from Ron Tatar of Crain Industries, Inc. to Dennis Curley re: Anti–Microbial Additives for Polyurethane Foam Undated, 1 Page.
Technical Data Sheet, Ultra–Fresh® DM–50 from Thomson Research Associates Undated, 4 Pages.

(List continued on next page.)

Primary Examiner—Peter M. Poon
Assistant Examiner—Elizabeth Shaw
(74) Attorney, Agent, or Firm—Rader, Fishman, Grauer & McGarry

(57) ABSTRACT

A mastication article for a domestic animal comprising tough chew-resistant material defining a shape in the form of a small article for enticing or being retrieved by a domestic animal, and an effective amount of microbe-inhibiting agent applied to or incorporated in the material. The mastication articles may be fabricated in various shapes, designs, and styles. A process for applying the microbe-inhibiting agent to the material for forming the mastication article is disclosed. Application methods include spraying and soaking the article, and incorporating the agent within a resin or material for forming the article. The article can be digestible in whole or in part.

94 Claims, 1 Drawing Sheet

U.S. PATENT DOCUMENTS

| | | | |
|---|---|---|---|
| 5,407,661 | 4/1995 | Simone et al. | 119/710 |
| 5,419,283 | 5/1995 | Leo | 119/710 |
| 5,467,741 | 11/1995 | O'Rourke | 119/710 |
| 5,474,033 * | 12/1995 | Mitchell, Jr. | 119/709 |
| 5,476,069 | 12/1995 | Axelrod | 119/710 |
| 5,477,815 | 12/1995 | O'Rourke | 119/710 |
| 5,485,809 * | 1/1996 | Carroll | 119/710 |
| 5,554,373 * | 9/1996 | Seabrook et al. | 424/400 |
| 5,711,254 | 1/1998 | O'Rourke | 119/710 |
| 5,845,769 | 12/1998 | Yeager | 206/204 |
| 5,857,431 | 1/1999 | Peterson | 119/710 |
| 5,868,933 | 2/1999 | Patrick et al. | 210/484 |
| 5,885,543 | 3/1999 | Klatte | 423/477 |
| 5,941,197 * | 8/1999 | Axelrod | 119/710 |

OTHER PUBLICATIONS

Antimicrobial Activity on Garments Undated, 2 Pages.

Milliguard, Retards the Growth of the Following Micro–Organisms, Undated, 2 Pages.

Fortrel Bactishield, The Antimicrobial Fiber Brochure Undated, 2 Pages.

Letter from C. Kel Little of Precision Fabrics Group, Inc. to Luis Didonato, Subject: Antimicrobial Undated, 1 Page.

Aegis® High Density Brochure Undated, 1 Page.

Effects of Microbial Growth in the Skin, Uniform Fabric Environment Undated, 2 Pages.

A New, Durable Antimicrobial Finish for Textiles*.

Richard L. Gettings, Dow Corning Corp., and Benny L. Triplett, Burlington Industries, Undated, 4 Pages.

Letter from Mike Sanders, Vice Pres. of Cal–Pacific Dyeing & Finishing Corp., to Luis Didonato of Lazy Pet, and attached speck sheet on the Durable Bacteriostatic and Fungistatic agent Undated, 2 Pages.

Vinyzene® Antimicrobial Additives for Plastics, Product Information Morton Plastics Additives, Undated, 2 Pages.

Vinyzene®, Material Safety Data Sheet Morton International, Inc., Dec. 18, 1996, 6 Pages.

Choose the Right Biocide to Meet Your Needs. Brochure on Cunilate® Morton Plastics Additives, Undated, 5 Pages.

Bio–Pruf™ Treated Brochure Morton International, Inc. Undated, 8 Pages.

Ultra–Fresh Brochure Undated, 2 Pages.

*Ultra–Fresh*\* Brochure Thomson Research Associates, Undated, 8 Pages.

\* cited by examiner

MASTICATION ARTICLE POSSESSING MICROBE-INHIBITING PROPERTIES

CROSS REFERENCE TO RELATED APPLICATIONS

This application is a continuation in part of application Ser. No. 09/241,591, filed Feb. 2, 1999 now abandoned and is a continuation in part of application Ser. No. 09/059,956, filed Apr. 14, 1998 abandoned which claims the benefit of U.S. patent application Ser. No. 60/043,014, filed Apr. 15, 1997.

BACKGROUND OF THE INVENTION

1. Field of Invention

This invention relates to a mastication article, principally for domestic animals, and more particularly to a mastication article having a microbe-inhibiting agent or property that substantially inhibits the proliferation of microbes on, within, or around the mastication article. The term "microbe" herein refers broadly to classes of bacteria, viruses, germs, molds, mildew, fungi, allergens, and other microorganisms. An article of the present invention provides both comfort and health benefits to both pets and people involved with the use of such an article.

2. Description of the Related Art

Mastication articles are very popular with pets, and especially so with dogs. There are two basic types of mastication articles: digestible and non-digestible. The prototypical digestible type is "rawhide" or rawhide-derived; but starch- or seed-based or other digestible materials may be used as well. The non-digestible type is more variegated, and may include alone or in part components comprised of molded plastic, rope, textile fabrics, fiber-fill, foam, as well as other components.

Mastication articles can provide therapeutic as well as amusement value to the pets that chew on them. The mastication provides a degree of exercise and cleans and massages the teeth and gums of the pet; and, pets (especially dogs) seem to enjoy mastication on things. In addition, giving pets desirable articles on which to chew may preclude them from mastication on other things that may be harmful to them or would upset the pet's owner.

Mastication articles for pets tend to become messy and unsanitary as the pets chew on them. There is also a risk of microbial proliferation on or within the mastication articles during their storage. Both of these factors are especially problematic for digestible mastication articles, which provide ample nutritional resources for the abundant proliferation of microbes. It is therefore useful and valuable to provide sanitary mastication articles that are resistant to the proliferation of microbes and optionally to odors. Because pets chew continually upon these articles, and because pets can eventually digest these articles (even when they are not intended for digestion), toxicity considerations with regard to the microbe-inhibiting treatment are important.

Of the digestible type, rawhide is the most popular type of mastication article. Ready-to-use rawhide may be acquired commercially in a variety of forms and is manufactured from animal (preferably cattle) hides by methods known in the Art (see, e.g., U.S. Pat. No. 5,114,704). The manufacturing process generally consists of several steps. After the raw hides are obtained, they are usually treated in a lime-based solution (liming), the primary object of which is to loosen the hair on the hide. To the solution may be added ammonium salts, sodium sulfide, or other additives. After the liming treatment, the hair is removed from the hide, either by hand or using a dehairing machine. In the next step, known as "fleshing," tissue is removed from the flesh side of the hide. This may be performed with a special knife or with a fleshing machine. It is then necessary to ensure that all of the lime is removed from the hide. Washing in water can remove much of the lime, but it is generally necessary to use a more aggressive treatment with acids or acid salts to remove the remainder.

After the hides are dehaired, fleshed, and cleaned, they may be cut into the desired shapes and manipulated. Drying may be done in ambient air or preferably in an oven at elevated temperatures (usually less than 150° C.).

U.S. Pat. No. 5,310,541 discloses a rawhide animal chew intended to inhibit oral pathogens from proliferating in a dog's mouth. The rawhide is treated with enzymes that are released into the dog's saliva upon mastication. Once in the dog's saliva, these enzymes set off a chain of reactions that attack oral pathogens present in the dog's mouth. Thiocyanate and iodide additives may optionally be added to enhance this effect.

U.S. Pat. No. 5,476,069 discloses a molded rawhide mastication article, in which rawhide is ground into small pieces and then injection molded at high temperature and pressure. The addition of casein and gelatin before injection are said to facilitate molding.

U.S. Pat. No. 4,419,372 discloses a simulated rawhide mastication article in which a mixture comprising an oil seed protein, a polyol plasticizer, lecithin, and water are extruded into a ribbon. The ribbon is then "sandblasted" (e.g., using ground walnet) to impart a rawhide-like texture to the surface. The material is then shaped or cut in a manner similar to those of real rawhides.

U.S. Pat. No. 5,407,661 discloses a digestible mastication article for a pet in which a starch, a cellulosic fibrous material (e.g., corn cob fractions), a humectant, a proteinacious binder and a tarter-control oral care additive are mixed together and extruded in such a manner that the extrudate possesses an open, cellular structure.

U.S. Pat. No. 5,419,283 discloses a molded mastication article for an animal comprising a starch material and a biodegradable ethylene copolymer. Other edible materials can be added as plasticizers or as lubricants. These materials are mixed in the presence of water for subsequent injection molding into desired shapes (e.g., a bone).

Mastication articles of the non-digestible type are considerably more variegated than those of the digestible type. They may be comprised of solid molded plastic, hollow molded plastic, textile fabrics, rope-materials, synthetic or natural fiber-fill, foams, etc. They generally possess a texture and structure that combine to create a desirable "mouth-feel" for the pet. This feature is especially important if the article possesses no attractants (e.g., a meat scent).

U.S. Pat. No. 4,557,219 discloses a molded polyurethane mastication article for a pet in which has been incorporated a surface-migrating flavoring extract.

U.S. Pat. No. 5,477,815 discloses a mastication article for a dog comprising a composite rope, in which an inner core of the rope comprises brittle, frangible, and non-water absorbing threads (optionally with a flavoring extract), and the outer shell comprises soft, pliable cotton. The inner core is said to give the article a "crunchy" sound and texture and to aid in the dog's passing of the article if it should be eaten. It is said that the non-water-absorbency of the inner core material promotes faster drying of the outer water-absorbing cotton material; and it thereby inhibits bacterial growth in the cotton. U.S. Pat. No. 5,467,741 discloses a similar mastication article, but includes the incorporation of therapeutic dental agents and/or breath-freshening agents in the inner core.

U.S. Pat. No. 5,477,815 discloses a molded bone-shaped mastication article that has relatively sharp, conically-shaped spikes distributed over its surface. The spikes are said to remove tartar or plaque from the dog's teeth as the dog chews on the toy. The mastication articles is a rigid polymer, such as a rigid polyurethane or a rigid polyamide. A meat scent or flavor is optionally added to the article to increase its attractiveness to dogs.

U.S. Pat. No. 5,477,815 discloses a molded dog mastication article which is constructed from a synthetic thermoplastic material (e.g., polyurethane) in which an animal meal (e.g., chicken meal, fish meal, etc.) has been incorporated prior the molding process.

U.S. Pat. No. 5,477,815 discloses a molded dog mastication article comprising water absorbing nylon in which at least a surface layer has been incorporated with sugar.

Despite the desirability of effective microbe-inhibiting mastication articles for pets, there have been no practical solutions that would provide effective and continual protection against microbial proliferation in or on the articles. The only two disclosures which even remotely relate to microbe inhibition are the aforementioned U.S. Pat. No. 5,477,815, which only relates to enhanced drying of a rope-based article to shorten the period of time it is most susceptible to microbial proliferation; and U.S. Pat. No. 5,310,541, in which the rawhide is a carrier for an enzyme to be released into a dog's mouth. In the latter invention, the rawhide is only a vehicle for delivering a reaction-initiating enzyme into the dog's mouth. The enzyme, which is inactive with respect to microbes, reacts with the salivary solution in the dog's mouth, ultimately resulting in the temporary creation of ions in solution which attack oral pathogens in the dog's mouth; and these ions can exist only in the dog's saliva. The rawhide article itself therefore contains no species that will inhibit subsequent microbial proliferation in and on the article (any such species which are transferred to the article from the dog's saliva will soon dry-up and thus become ineffective).

Thus, there is a need in the art for mastication articles for pets, where the proliferation of microbes is prevented in and on the articles; where the microbe-inhibiting properties of the articles are continually active and durable; where these articles are desirable and attractive to the pets for which they are intended; and where these articles are safe for pets and humans.

SUMMARY OF THE INVENTION

According to the invention, mastication articles for pets have an effective of amount of microbe-inhibiting agent or property that is effective in limiting microbial proliferation, and at the same time is not present in quantity, concentration, or nature whereby the articles may be harmful to the pets or humans who come into contact with the articles. The effective amount of the microbe-inhibiting agent or property limits the spread of the microbe-inhibiting chemicals or agents within and about the article, and takes into consideration the patterns of use and material structure of the article. The microbe-inhibiting agent or property can be at least one of a microbe-cidal, microbe-starving, and microbe-impenetrable agent. In one embodiment, a digestible mastication article is selected from a group consisting of animal skin, animal fat, vegetable, a vegetable starch or some blend thereof. In another embodiment, a non-digestible mastication article comprises at least one material selected from a group consisting of polymeric resins or solutions, fibers or threads, textile materials, foams, or some blend thereof.

Another embodiment of a mastication article includes a microbe-inhibiting agent as a particulate incorporated into the material comprising core particles over which is coated with a microbe-inhibiting active layer. The core particles are selected from the group comprising zinc oxide, titanium. barium sulfate and blends thereof. The active layer is selected from a group consisting of silver, copper oxide, zinc silicate and blends thereof. In a further embodiment, the active layer includes a barrier coating, whereby the rate of release of the microbe-inhibiting agent or property can be controlled. Also, the active layer can include a dispersion coating, whereby the core particles in the material are dispersed.

In another embodiment of the invention, the mastication article comprises rope, wherein the rope can be made of at least one material selected from a group, cotton, sisal, hemp, jute, henequen and blends thereof. Furthermore, the mastication article made from rope can include a core made of a hydrophobic material such as nylon.

In another embodiment of the invention, the mastication article is made of at least one material selected from the group including nylon, polyurethane, polyolefins and blends thereof. Such a mastication article can include a nutritive attracting agent within the material. Such a nutritive attracting agent is preferably selected from the group including animal meal, meat broth, dried meat, sugar and blends thereof.

Further, according to the invention, a method for producing a mastication article having a tough, chew resistant material and defining a shape in the form of a small article for enticing or being retrieved by a domestic animal comprises the step of applying an effective amount of a microbe-inhibiting agent to the tough, chew resistant material. The microbe-inhibiting agent can be applied to the tough, chew resistant material by dissolving the agent in a solution, which is then applied to the tough, chew resistant material, either by soaking the tough, chew resistant material in the solution or spraying the solution onto the tough, chew resistant material.

In one embodiment, the microbe-inhibiting agent is in particulate form and is incorporated into core particles in the article. The core particles are selected from a group including zinc oxide, titanium oxide, barium sulfate and blends thereof. The process can include the additional step of incorporating the particles into a resin that is molded into the tough, chew resistant material. Alternatively, the particles can be incorporated into a dope before spinning of fibers that are incorporated into the tough, chew resistant material. In a further embodiment, the particles are incorporated into a spray for coating an outer surface of the tough, chew resistant material.

In another embodiment, the tough, chew resistant material is rawhide and the step of applying the microbe-inhibiting agent includes applying the microbe-inhibiting agent to the rawhide during cleaning of the rawhide. Alternatively, the microbe-inhibiting agent can be applied to the rawhide during liming of the rawhide.

In yet another embodiment, the microbe-inhibiting agent is incorporated into the tough, chew resistant material by applying a solution including the agent to the material. In one embodiment, the tough, chew resistant material is digestible and the microbe-inhibiting agent is added to the tough, chew resistant material when the material is in a molten or substantially liquid state, and the material is then molded to form the article. In a first variation of this process, the step of incorporating the microbe-inhibiting agent includes applying the solution to the tough, chew resistant material after the article has been formed. In another variation, the microbe-inhibiting agent is incorporated into the material by soaking the tough, chew resistant material in the solution after the article has been formed. For articles including digestible components, a first variation includes the anti-microbial agent is selected from the group consisting of triclosan, diiodomethyl-p-tolylsulphone, tri-n-butyltin maleate and chlorine dioxide. Commercial forms of the first three of these are available under the trade names Ultrafresh NM-100, UF-95, and DM-50, respectively). In another variation, the agent is selected from the group consisting of garlic and turmeric.

In any of the processes described above, a nutritive attracting agent imparting a flavor or smell to the mastication article can be incorporated into the tough, chew resistant material. Furthermore, for any of the processes set forth above, the microbe-inhibiting agent can be applied to the tough, chew resistant material at a temperature between 40–100° Celsius.

For a mastication article comprising cotton rope, a process according to the invention includes a step of applying moisture to the cotton rope as it is being formed, and then spraying the cotton rope with a solution including the microbe-inhibiting agent to enhance the absorptive properties of the cotton rope.

Where the process according to the invention includes forming the mastication article of a material including fibers, the application of the microbe-inhibiting agent can be accomplished by incorporating the agent into a doping agent for the fibers and then spinning the fibers.

Where the process according to the invention includes molding the mastication article, the step of incorporating the microbe-inhibiting agent can include adding the microbe-inhibiting agent to a resin and then molding the resin into the mastication article.

In one embodiment, the tough, chew resistant material can be formed from a latex mixture that is molded into the tough, chew resistant material and the microbe-inhibiting agent can be added to the latex mixture before the molding step.

DETAILED DESCRIPTION OF THE INVENTION

Figure 1:
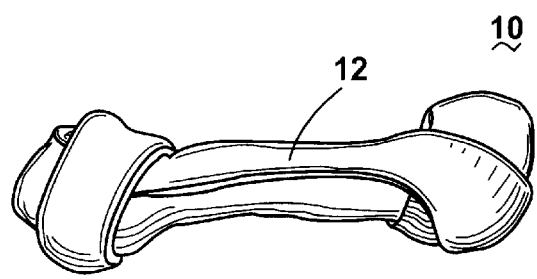
FIG. 1 is perspective view of a first embodiment of a mastication article according to the invention.
Figure 2:
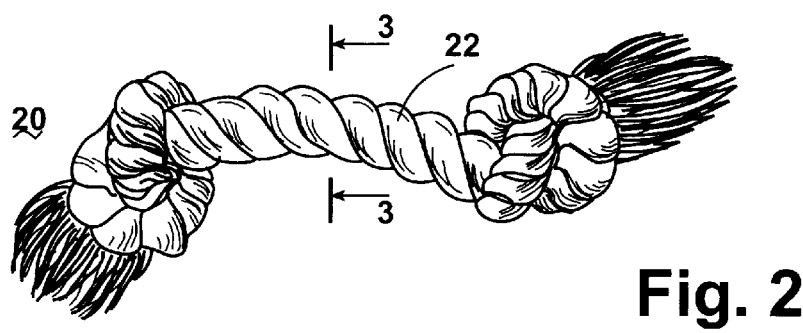
FIG. 2 is perspective view of a second embodiment of a mastication article according to the invention.
Figure 3:
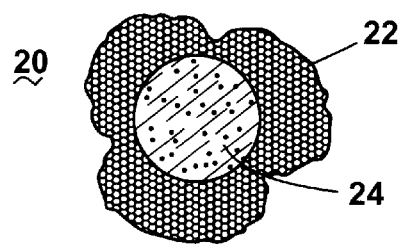
FIG. 3 is a sectional view the mastication article of FIG. 2.
Figure 4:
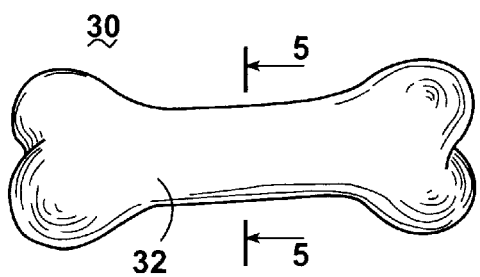
FIG. 4 is a perspective view of a third embodiment of a mastication article according to the invention.
Figure 5:
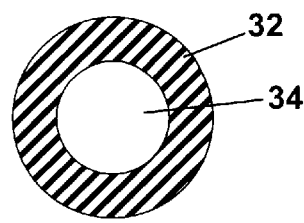
FIG. 5 is a sectional view of the mastication article of FIG. 4.

Referring to FIGS. 1–5, several embodiments of a mastication article are shown. In FIG. 1, a first embodiment of a mastication article 10 made of a tough chew-resistant rawhide material 12 is shown. The rawhide material 12 includes a microbe-inhibiting agent applied to or incorporated therein, as will be discussed further below. A second embodiment is a mastication article 20 made of a rope material 22, as shown in FIG. 2. The rope material 22 preferably comprises cotton, and is treated with a microbe-inhibiting agent as will be described below. As shown in FIG. 3, the mastication article 20 may include a core 24 comprising a different material, usually a hydrophobic material such as nylon. FIG. 4 shows another embodiment of a mastication article 30 made of a plastic material 32. The mastication article 30 may be hollow, having a open center 34, as shown in FIG. 5, or solid (not shown), and is treated with a microbe-inhibiting agent during formation, as will be described below.

The term "microbe-inhibiting" in the present disclosure subsumes all characteristics (and the means for imparting these characteristics) which cause the mastication articles to be inhospitable to microbes. Distinctions can be made between three types of microbe inhibition:

"Microbe-cidal" refers to a property whereby microbes are actively killed or otherwise rendered ineffective. If a microbe comes within a sufficiently close range (direct contact, for some materials; within a "zone of inhibition" for others ) of a microbe-cidal material, it will be killed or otherwise rendered ineffective. Microbe-cidal properties may be imparted to materials by a variety of means. A preferred means uses microbe-cidal agents during the manufacturing process of the materials and/or treats the materials with microbe-cidal agents. A number of preferred agents are disclosed below. For the microbe-cidal property to be durable, it is often preferred that the agents be bonded in some manner to the materials comprising the pet article. Such materials exhibit smaller zones of inhibition than materials containing non- or weakly bonded agents, but the microbe-cidal property with regard to microbes coming directly into contact with the material can be more durable. Using agents which are insoluble or only sparingly soluble in water can also be a key element for durability.

"Microbe-starving" refers to a property whereby microbes are controlled or eliminated by deprivation of sources of nutrition. A material is said possess microbe-starving properties if microbes in contact with the material have difficulty acquiring the resources they need to survive. One can often provide or enhance a microbe-starving characteristic to a material by changing or altogether eliminating additives to the materials (e.g., plasticizers, fillers, or processing aids). Since adhered dust or liquids can provide nutrition for microbes, it is preferred that the material be provided with anti-adhesion properties (e.g., anti-static, low surface energy, etc.).

"Microbe-impenetrable" refers to the property of a material or coating which is impenetrable whereby a microbe cannot pass through the material or coating. In this case, microbes may proliferate to some degree on a surface of the material, but such proliferation will be confined to the surface. Thus if an article is treated on its exterior by a microbe-impenetrable coating, microbes from the environment will not be able to pass into the interior of the article, will be limited in the degree to which they can proliferate, and can more readily be removed by washing. Appropriate placement of microbe-impenetrable materials is important to their effectiveness in providing the microbe-inhibiting property.

It is often efficacious to fight the battle against microbial proliferation on several fronts. Thus preferred microbe-inhibiting mastication articles for pets will often possess combinations of microbe-inhibiting behavior. For example, when a particular component of a mastication article is most susceptible to microbial attack, this component may be treated with both a microbe-impenetrable layer and a microbe-cidal agent, while the remainder of the article is treated with only the microbe-cidal agent. Further, an additive which serves as a resource for microbial growth may be important only for certain parts of the article. For example, plasticizers often act as an effective resource for microbial proliferation; and one can use the plasticizer only where the flexibility is needed, and then treat this area with an effective combination of microbe-inhibiting characteristics; and the remainder of the article, where the plasticizer was not used, may be less vigorously protected.

For durability, the microbe-inhibiting agents should not readily dissolve into the fluids with which they come into contact. This includes fluids associated with their use (saliva, urine, or other bodily fluids) as well as washing and cleaning fluids (the microbe-inhibiting activity should be durable to repeated home laundering). The insolubility may be an intrinsic characteristic of the agent-fluid combination, or it may be due to the fact that the agents are well bonded to the materials comprising the article. Both types are included in the present invention.

Although both water-durable and non-water-durable microbe-inhibiting components can be used with effectiveness in the present invention, if a non-water-durable microbe-inhibiting component is used, the exterior of the exposed material should desirably be provided with water-repellent or otherwise water-insulating qualities.

In a preferred class of embodiments, microbe-inhibiting properties are conferred upon one or more of the materials comprising the pet article by treating the material with or otherwise incorporating into the material a microbe-inhibiting agent. This microbe-inhibiting agent is a chemical agent or particle that imparts to the material an effective microbe-inhibiting property. The microbe-inhibiting agents will often function primarily through a microbe-cidal mechanism. The microbe-inhibiting agents are typically chemicals, polymers, solutions (solid or liquid), or particulates (which may possess their own microbe-inhibiting activity or can act as hosts for other microbe-inhibiting agents). These microbe-inhibiting agents can exist in a variety of forms and be held in a variety of hosts before being incorporated into the mastication article. For example, they can be dissolved in a liquid; they can be incorporated in or form a particulate phase, either dry or suspended in a liquid; they can be included within a plasticizer compound; or they can be pre-incorporated into a material used in manufacturing the article (e.g., one can employ materials which already possess microbe-inhibiting properties).

Examples of chemical microbe-inhibiting agents for use in polymers may be found in *Plastics Additives and Modifiers Handbook,* pp. 338–350, J. Edenbaum, Ed., Chapman and Hall, Great Britain, 1996, and herein incorporated by reference.

The microbe-inhibiting treatment can be carried out at different points during the process of manufacturing the article or its component materials. For example, one can incorporate microbe-inhibiting agents in fibers as they are being manufactured, which microbe-inhibiting fibers can be used as the filling of stuffed mastication articles or as the fabric used as the external covers of mastication articles. One can also manufacture a microbe-inhibiting elastomeric-like material for use in a component of the mastication article which is made of (e.g., molded) plastic. One can also treat (as by spraying or soaking) some or all of the materials after they are partially or completely manufactured (e.g., one can soak rawhide sheets or the rope which will be later cut and formed into rope-bones in a microbe-inhibiting treatment solution; or one can treat the external cover and/or the filling or some component of the filling of a mastication articles before their final assembly). Alternatively or in addition, one can treat (as by spraying or dipping) the pet article when it is finished or nearly finished its manufacture. It is often preferred to perform soak treatments under elevated temperatures and/or pressures.

Microbe-inhibiting agents can be incorporated into the constituent material(s) of a mastication article by admixing the agent or a carrier for the agent with the raw ingredients to the material (e.g., add a liquid containing the agent to the resin mix before injection molding a plastic article). In this case, the microbe-inhibiting agent is usually dispersed relatively uniformly throughout the final article.

In cases where surface attachment is desired, the use of adhesion promoters is preferred, particularly in conjunction with "raw" microbe-inhibiting agents, i.e., those which do not need to be in solution to work effectively.

In cases where a bonding agent is not used to adhere the microbe-cidal agent to the mastication article material, or where such bonding is not entirely effective, it is often useful to diminish the rate at which the active microbe-inhibiting agent becomes de-activated. This process can be done by inhibiting volatilization or adding stabilizers.

When the microbe-cidal agents are not bonded or are only weakly bonded to materials forming the mastication article, it is preferred to package the articles such that the effective shelf life of the antimicrobial character is enhanced. For example, when volatilization of the antimicrobial agent is a problem, the packaging material can be made impervious to the antimicrobial agent.

It is useful to have a microbe-inhibiting agent at the surface of the mastication article, as well as in the interior. The microbe-inhibiting agent at the surface can be effective in inhibiting the proliferation of microbes directly on the surface. If suitable microbe-inhibiting agents are present in the interior, they can migrate to the surface as the agent initially at the surface becomes displaced. This effectively constitutes a "time-release" of microbe-inhibiting agent. In this manner, the concentration of the agent can be maintained at a safe level, any odors associated with unduly high concentrations of the agent are avoided, and the period of effective microbe-inhibiting protection can be considerably prolonged.

The microbe-inhibiting agent can be applied in a liquid form (as dissolved in a solvent) and deposited on the surface of the mastication article material. By choosing properly the liquid, material, environmental conditions (e.g., temperature, pressure) and optionally any additives, the agent can be made to penetrate the material; and a "time-release" system can be obtained.

A "time-release" property may also be provided by incorporating the active agent in a separate material, optionally particulate, which releases the agent in a time-controlled manner. For example, one can saturate a particulate zeolitic material with a microbe-inhibiting agent and incorporate the zeolitic material into the pet article. Alternatively, one can use a textile chosen specifically for its time-release characteristics for a particular microbe-inhibiting agent; and this textile may be incorporated in the mastication article.

If some form of heat-assisted disinfection of the articles is desired, it is important to use material-agent systems which do not degrade in the disinfection environment (e.g., washers, microwave, thermal ovens, etc.). The softening or decomposition temperatures of the polymers and chemical agents used, for example, must be higher than the disinfection temperature used.

Because the accumulation of undesired organic or inorganic matter may reduce the efficacy of microbe-inhibiting protection, the articles can be designed with materials which reduce the tendency for such accumulation. This can be accomplished by using low surface energy materials or applying a low surface energy coating; and/or by using anti-static materials or applying an anti-static coating. Non-hydrophilic materials (materials upon which water droplets form contact angles greater than about 30 degrees) are generally preferred to prevent the adhesion of such undesired matter.

Pets, especially dogs, often tear or otherwise damage or digest the mastication articles that they use. It is therefore important that the materials be non-toxic, non-carcinogenic, and effectively non-allergenic at the levels used in the articles. Some agents are non-toxic even at relatively high concentrations (e.g., triclosan, diiodomethyl-p-tolylsulphone, stabilized chlorine dioxide); other agents are non-toxic at relatively low concentrations, but become toxic at high concentrations (e.g., many unbonded quaternary ammonium compounds). If a mastication article employs a time release property, one must ensure that the time-releasing materials do not contain concentrations of the agents which exceed those which can be safely eaten by the animal of interest. The pet should be able to eat the article without harm. Also, the treated materials should be non-skin-sensitizing, i.e., should not generally cause allergic or other undesirable reactions on the skin or other membranes of the pet or people who effectively come into contact with the materials.

Preparation of Materials

Unless otherwise stated, concentrations given herein are weight percent.

Materials of the present invention can be made from natural animal products, including skin and fat-based materials, natural vegetable products, polymeric resins or solutions, fibers or threads, textile materials, foams, and other materials. At least some fraction of the constituent materials has microbe-inhibiting properties.

In preparing microbe-inhibiting synthetic materials derived from polymers, the microbe-inhibiting agents are preferably added to the precursor material (e.g., into the resin mix for molded plastics or into the melt or spin dope from which fibers are spun). For natural materials, the microbe-inhibiting agents are preferably either impregnated into the materials via a spray or soaking treatment. Microbe-inhibiting agents or carriers with such agents can also be included in an admixture of natural and/or synthetic materials that are to be transformed into the finished article.

Phenol derivatives, especially 2,4,4'-trichloro-2'-hydroxydiphenol (known as Triclosan, Irgasan, Microban, etc.) are attractive and are preferred. Methyl sulfones, such as diiodomethyl-p-tolylsulphone, are attractive and preferred. Organotins, especially tri-n-butyltin maleate (as in Ultra Fresh DM-50), are also attractive and preferred. Soak-treating in an aqueous solution containing stabilized chlorine dioxide is also preferred.

It is important to note that post-treatment methods involve importantly different considerations when one is using a "strongly-bonded" type of agent. In the "diffusing" or "nonstrongly-bonded" case, one immerses or otherwise exposes the materials to a solution containing a particular concentration of the agent. Generally, the agent diffuses into the material until its concentration in the material is comparable to the concentration in the solution, i.e., the treatment level of the material is essentially proportional to the concentration of the agent in solution; and the agent concentration in the solution is the primary controlling variable. In typical treatments, the agent in solution is not appreciably depleted; and the amount of material exposed to the treatment solution is not carefully monitored and is not considered a primary variable of the treatment process.

In the strongly-bonded case, however, the agent usually does not diffuse into the material; rather, it chemically reacts with the surface of the material. Here one attempts to arrange conditions such that most of the "reactable" agent present in the solution reacts with and bonds to the surface of the material being treated. Knowledge of the amount of material being treated is thus important in determining the treatment level; and the material amount, along with the agent concentration in solution, are considered controlling variables of the treatment.

The term "amount of material," is intended to mean the "amount of reactable surface" of the material. For porous materials which can take up the solvent in their interiors (e.g., many natural materials such as cotton or rawhide, fabrics, foams, etc.), the mass of the material is often used as an indicator of the reactable surface area—i.e., one can specify an agent level in solution per unit weight of material being treated. For non-porous materials and/or materials which do not absorb the solvent being used (hard plastics, highly solvent-phobic materials), more direct knowledge of the reactable surface area is needed.

The preferred strongly-bonded agent for use in the present invention is 3-trimethoxysilylpropyldimethyloctadecyl ammonium chloride (as in Dow Corning 5700).

For use in mastication articles that contain fabrics, microbe-inhibiting fabrics can be constructed by weaving, knitting, or otherwise forming the fabric from fibers which possess the desired microbe-inhibiting properties. Alternatively, the fabrics can be post treated via spray-treating or by using a padding system such as are common in the art of textile finishing. For post treatment, tri-n-butyltin maleate (as in Ultra Fresh) is a preferred diffusing microbe-inhibiting agent (at fabric pick-up about 0.1%–0.5% by weight); and 3-trimethoxysilylpropyldimethyloctadecyl ammonium chloride (as in Dow Corning 5700) is a preferred strongly bonded microbe-inhibiting agent (at fabric pick-up about 0.08%–0.15% by weight).

The preferred method for obtaining microbe-inhibiting foams is to include a microbe-inhibiting agent in the formulation of one of the foam precursors (i.e., before the material is foamed). A preferred microbe-inhibiting foam is obtained by adding Ultra Fresh DM-50 to the polyurethane foam formulation before foaming (typically in amounts ranging from 0.04% to 0.6% relative to the total weight of the formulation). Another preferred method is to use Dow Corning 5701 (a reactive silane quaternary ammonium compound, which works much like Dow Corning 5700). This agent is also added into the polyurethane formulation before foaming (typically in amounts ranging from 0.1% to 1.2% by weight relative to the amount of polyol).

Another preferable microbe-inhibiting agent is known by the trade name, Intersept. It is a complex of polysubstituted imine salts and trialkyl phosphate esters with free alkylated phosphoric acid. It is relatively non-toxic; and it has been used as an antimicrobial finish on many building materials.

A further preferred type of microbe-inhibiting agent is typified by the MicroFree brand of particulates (available from DuPont). These particulates generally comprise a core particle (zinc oxide, titanium oxide, or barium sulfate) over which is coated a microbe-inhibiting active layer (silver, copper oxide, and/or zinc silicate). A barrier layer (to control the rate of release of the active component) and a dispersion coating (to facilitate dispersion of the particles in host materials) are included on top of the active layer. The particles range from about 0.3 µm to 1 µm in size. They can be incorporated into many resin systems for plastics processing, into the dope before fiber spinning, and into many coating systems for post-treatment. Good microbe-inhibiting efficacy can be imparted to various materials using these particles; and the resulting materials are generally non-toxic, very stable, and cost effective.

Other microbe-inhibiting agents may be used without departing from the spirit of the present invention.

Rawhide Mastication Articles

For rawhide mastication articles, microbe-inhibiting characteristics can be imparted to the rawhide by treating it with microbe-cidal agents as defined above during the process of manufacture. This treatment can be carried out during the liming or one of the cleaning phases; or an additional step can be added in which the hides are sprayed with or soaked in a microbe-cidal solution.

The rawhide can also be treated after it is essentially fully manufactured. In its "hard" form, it can be sprayed with a microbe-cidal solution (which can be allowed to soak-in), or it can be soaked in a microbe-cidal solution for a time sufficient for the microbe-cidal agents to infiltrate appreciably the rawhide. In the latter case, it will generally be necessary to dry the treated rawhide (in ambient air or in a furnace at elevated temperature).

It is necessary to ensure that the processing temperature, either during or after the microbe-inhibiting treatment, is not excessively high so as to inactivate or otherwise damage the microbe-inhibiting properties of the article.

Because dogs often eat rawhide, toxicity considerations are important. A preferred agent for use with rawhide products is chlorine dioxide, which is safe for both animal and human consumption (e.g., it is used in mouthwashes, toothpaste, and as a drinking-water additive). An appropriate solution concentration is in the range of about 0.1–2% by weight.

Also preferred is diiodomethyl-p-tolylsulphone. A commercially available form is available under the name Ultrafresh UF-95. It is generally desired to treat the rawhide so that the concentration of UF-95 is between 0.001% and 2%, preferably between 0.05% and 0.8% by weight. An alcohol, preferably ethanol, is the primary solvent of the preferred treatment solution. Acetone, in which the agent possesses a larger solubility than in ethanol, can also be used (provided the acetone does not persist substantially in the finished articles). When treating by soaking in such non-aqueous solutions, subsequent rinsing in an aqueous solution is preferred.

Also preferred is tri-n-butyltin maleate. A commercially available form is available under the name Ultrafresh DM-50. Water is the primary solvent for the preferred treatment solution, which contains between 0.005%–0.4%, preferably 0.008%–0.1% by weight of the DM-50 agent.

Also preferred is triclosan. It is generally desired to treat the rawhide so that the concentration of triclosan is between 0.01% and 1.2%, preferably between 0.05% and 0.6% by weight. An alcohol, preferably ethanol, is the primary solvent of the preferred treatment solution. When treating by soaking in a triclosan solution, subsequent rinsing in an aqueous solution is preferred.

It is generally preferred to treat the rawhide during its manufacture, i.e., before the final drying step. In some cases, it is preferred to post-treat finished rawhide. First, one must "open-up" the rawhide structure. This is done by soaking the rawhide in water or other suitable non-toxic solvent (e.g., ethanol). The "opened" rawhide is then placed in the desired treatment solution for soaking. After sufficient time has elapsed for the rawhide to absorb an efficacious level of the microbe-inhibiting agent, it is removed from the treatment bath and dried. If the opening solvent and the treatment solvent are the same, one can combine the two steps (i.e., the treatment solution will serve also to open-up the rawhide).

Adding an amount (typically 0.1–20% by weight) of a soluble or dispersible polymer or organic material to the treatment solution can assist in the retention of the microbe-inhibiting agent in the rawhide. For example, one can incorporate many cellulose ether materials (e.g., methyl cellulose, hydroxyethyl cellulose, or carboxymethyl) or poly (vinyl alcohol) in water-based solvents. Starches, agar, gelatin, casein, lard, etc. can also be useful. Butyl cellulose, among others, is soluble in ethanol, a preferred solvent for triclosan and diiodomethyl-p-tolylsulphone. Preferred microbe-inhibiting agents to be used with retention-assisting ingredients are triclosan, diiodomethyl-p-tolylsulphone, and Ultra Fresh DM-50, and chlorine dioxide. When retention aids are used in this manner, one must ensure that both the retention aid and the microbe-inhibiting agent are sufficiently soluble or dispersible in the solvent.

According to one embodiment of the invention mastication articles such as rawhide can be molded. Molded rawhide articles are formed by initially cutting or shredding conventional rawhide into small pieces. This process is often facilitated by first soaking the rawhide in a good solvent, such as water. It is often preferred to boil the rawhide in water before cutting it. The small pieces should then be dried.

These dried small pieces can then be admixed with additives designed to give the final product an improved "mouth feel." Casein, agar, gelatin, sugary syrups (e.g., honey) are examples; they are typically added in amounts less than about 10% by weight based on the weight of the final article.

The microbe-inhibiting agent is then added to this admixture. A preferred agent is triclosan, added in a quantity such that its concentration in the finished product is between 0.001% and 1%, preferably between 0.004% and 0.1% by weight. It is frequently preferable to dissolve the triclosan in a solvent before adding it to the mixture; the preferred solvent is ethanol. Diiodomethyl-p-tolylsulphone, as in UF-95, is also preferred. It should be added in a quantity such that its concentration in the finished product is between 0.001% and 2%, preferably between 0.01% and 0.8% by weight. It is sometimes preferable to dissolve the agent in a solvent before adding it to the mixture; the preferred solvent is either ethanol or acetone. Ultrafresh DM-50 is also preferred, added in a quantity such that its concentration in the finished product is between 0.001% and 1%, preferably between 0.004% and 0.1% by weight. It is frequently preferred that the DM-50 be carried in a solvent, preferably water.

Chlorine dioxide dissolved in solvent is also preferred, added in a quantity such that its concentration in the finished product is between 0.0001% and 0.5%, preferably between 0.001% and 0.2% by weight.

The admixture is typically pre-heated to burn off a large part of the remaining solvents. The admixture is then fed into an injection molding machine under elevated temperature and pressure. It is desired that liquification occur. This generally requires pressures in excess of 60 atm and temperatures in excess of 120° C. Pressures and temperatures in the environs of 75 atm and 145° C., respectively, are preferred. Desired shapes are then molded.

Microbe-inhibiting molded rawhide can also be manufactured using other techniques. For example, one can obtain finely divided rawhide by boiling the rawhide; cutting it into small pieces; soaking the pieces in ethanol; drying the pieces in an oven; and grinding the rawhide in a coffee bean grinder. This finely divided rawhide can then be mixed with the desired microbe-inhibiting agent, a solvent, agar (or other degradable polymer), and optional flavoring additives. The mixture can be heated until it is quite thick, and then poured into a mold. Subsequent heating will further dry and congeal the product into a rawhide-based mastication article. Articles of this type, however, are generally much less tough than the injection-molded type.

It is also useful to provide a spray bottle or the like containing microbe-cidal solution which the pet owner can apply periodically to the rawhide to refresh its microbe-inhibiting properties. In this case, an aqueous solution of chlorine dioxide (with concentration about 0.083%) is preferred. Ethanol solutions, used with sufficiently low frequency and at sufficiently low concentrations so as not to affect adversely the animal, are also useful for this purpose. Other "natural anti-microbials" can also be used.

Mastication Articles Containing a Digestible/Degradable Component

According to one embodiment of the invention, mastication articles made at least in part from materials containing a digestible/degradable component. Pets can derive pleasure from chewing them, and the pets can eventually digest them. Ideally, the articles are sufficiently dense and slow to absorb water that they retain their mechanical integrity and "chewability" for a significant period of time before they become very soft; and they exhibit a significant element of reversibility in characteristics upon drying.

Such articles rarely comprise only starch, since pure starch tends to be brittle and is difficult to process. Starch is typically blended with other polymer materials and/or with materials that serve as plasticizers. Common polymer blending materials include poly-ethylene-acrylic acid or poly-ethylene-vinyl alcohol (see U.S. Pat. No. 5,419,283, which is hereby incorporated by reference). Other common blending materials include polyethylene, polypropylene, polystyrene, polyvinyl chloride, polyurethanes, polyesters, polyamides, polyacrylates, polyethers, polyisoprene, rubbers, and polylactides. U.S. Pat. No. 5,446,078, which is hereby incorporated by reference, describes the reactive blending of such materials with starch materials.

Common plasticizers include sorbitol, glycerol, sucrose, and fructose. These are typically added in amounts ranging from 1% to 20% by weight. Water can also serve to some degree as a plasticizer.

A shortcoming of prior mastication articles is that such digestible/degradable articles are extremely susceptible to the proliferation of microbes. This problem is especially true of such articles based on corn starch such as described in U.S. Pat. No. 5,419,283 and available commercially from Novamont under the mark Mater-Bi). In fact, a Mater-Bi cornstarch-based article purchased commercially and submerged in tap water for several days can give rise to dramatically visible proliferation of microbes.

Despite the fact that such articles have been on the market for years, no solution has been proposed to combat the problem of microbial proliferation in and on articles constructed using digestible polymers. It is therefore especially attractive to construct such digestible articles such that they will not support the growth of microbes.

Generally speaking, the anti-microbial agent(s) can be incorporated into the material(s) which will comprise the digestible/degradable mastication article when the material or blend of materials are in a molten or substantially dissolved state, or they can be incorporated into one or more of the constituent raw materials at the time of forming of these raw materials. Alternatively, the anti-microbial agent(s) can be mechanically mixed with the constituent raw material(s) before these materials are formed into the final article. In addition, the anti-microbial agent(s) can be included in a treatment solution to which the articles are exposed or to which the raw material is exposed prior to being used to form the articles. In this latter case, it is preferred to soak the articles in the treatment solution (rather than to spray or expose to the vapor).

A preferred method is to incorporate the anti-microbial agent(s) into one of the polymeric raw materials with which the starch is blended. This incorporation should generally take place at the time of compounding of the polymeric raw material. The concentration of the anti-microbial agents(s) in the polymeric raw material must be such that the ultimate concentration in the overall blend is as desired (i.e., the polymeric raw material must be overloaded). Preferred ultimate concentrations are given below.

One may use synthetic or natural microbe-inhibiting agents to provide the desired properties to these articles. Synthetic agents are generally preferred for articles which are intended primarily for purposes of mastication, although, especially since these articles are often at least in part consumed, natural agents can also be used. Natural agents are generally preferred for articles that are intended primarily or exclusively for purposes of consumption by the animal.

A preferred synthetic agent is diiodomethyl-p-tolylsulphone (see "Microbicides for the Protection of Materials," by Wilfried Paulus, 1993, Chapman & Hall, which is hereby incorporated by reference, for data on this and other biocidal/biostatic agents). This agent possesses a broad spectrum of anti-microbial activity, and it is most active against fungi, yeasts, and algae. This agent is especially preferred in applications where the article may be partially or wholly digested or in cases where the article is in contact with materials which are to be digested. This agent can cause yellowing in the final material, and if this is deemed as unattractive, it may be used in conjunction with color suppressants. The agent melts at about 157 C. It is relatively insoluble in water (0.0001 g/l at 25 C). Acetone (350 g/l at 25 C) and ethanol (20 g/l at 25 C) are preferred solvents. The agent is generally stable in the pH range of 4–10. A preferred form of the agent is Ultrafresh UF-95, available from Thomas Research Associates. The concentration of UF 95 in the finished product should be between 0.001% to 3%, preferably between 0.01% and 1%. Another preferred synthetic agent for incorporation into articles possessing a digestible component is Irgasan DP300 (triclosan). It should be used in a quantity such that its average concentration in the finished product is between 0.001% and 1%, preferably between 0.004% and 0.1% by weight. Ethyl alcohol is a preferred solvent for triclosan. Ultrafresh NM-100 (available from Thomas Research Associates) is another preferred form of triclosan, added in a quantity such that its concentration in the finished product is between 0.001% and 2%, preferably between 0.004% and 0.3% by weight.

Triclosan melts at about 60° C., and decomposes at about 285° C. The fact that triclosan melts at 60° C. facilitates the mixing of the triclosan with other raw materials, especially when such materials are in a powder form; and much flexibility in processing is achieved in the large window between melting and degradation.

Chlorine dioxide is also preferred, added in a quantity such that its concentration in the finished product is between 0.0001% and 0.5%, preferably between 0.001% and 0.2% by weight. Water is a preferred solvent.

As noted earlier, in many cases, articles based on biodegradable materials, especially starch-based biodegradable materials, may be designed expressly as food items (in contrast to mastication articles that may be digestible or have a digestible component). In this case, the need for a microbe-inhibiting property is acute, since, in sharp contrast to human foods, people do not usually exercise the proper care to ensure that the articles are stored and transported properly before use. It is generally preferred in such cases to incorporate natural anti-microbial agents or food preservatives agents (or their oils) into mastication materials. These anti-microbial agents include garlic, turmeric, or other spices known to be inhospitable to microbes. Common food agents such as sugar and salt may be used to make the articles less susceptible to microbial proliferation. A variety of compatible preservatives and their properties are described in Disinfection, Sterilization, and Preservation, Edited by Seymour S. Block (Lea & Feniger, 1991), which is herein incorporated by reference.

It is preferred to comminute these natural microbe-inhibiting materials to some degree before incorporation into the base material. It is further preferred to incorporate the natural antimicrobial materials into the raw material and then use the raw material in the usual manner to produce the articles.

Alternatively, one can include the comminuted material with the mix of other raw materials before molding the articles (e.g., add to the hopper before injection molding). Treatment may also be carried out by soaking, optionally under high pressure, the molded articles in a solution or broth containing the natural microbe-inhibiting materials.

In some cases (e.g., with garlic-based microbe-inhibiting agents), consumption by the animal can result in bothersome halitosis. If this is perceived as a problem, it is preferred to treat the natural microbe-inhibiting material in such a way as to derive an extract or broth which possesses the desired microbe-inhibiting quality but does not cause halitosis. Since many natural anti-microbial materials are believed to possess therapeutic properties for humans, there are many known methods to produce such extracts (e.g., U.S. Pat. No. 5,391,390, which is herein incorporated by reference).

Natural anti-microbial agents are often perceived by people in a more favorable light because they are "natural." In addition, they can also be preferred because they are frequently, at least in part, water soluble. This property facilitates incorporation of these materials into many biodegradable materials, such as the starch-based materials, which possess a significant degree of solubility with respect to water (in contrast to triclosan or diiodomethyl-p-tolylsulphone, which are not readily soluble in water). It is often preferable to use a biodegradable material—microbe-inhibiting agent combination which possess a common solvent).

Although articles constructed from many polymers containing a digestible component, such as those based on Mater-Bi, are in fact digestible, they may not provide sufficient enticement for the pet to chew on them. For this reason, it is preferred to add enticing additives, such as flavorings or scents, to the articles. For example, an amount of catnip or catnip oil can entice a cat to chew or otherwise be attracted to the article. Comminuted catnip, for example, can be added to the hopper with the raw materials.

Similarly, a fish scent or fish-flavored additive may encourage the cat to chew on the article. Meat scents or flavorings are particularly attractive for dogs.

It is further desirable to incorporate components into the chewing articles which impart a therapeutic quality. For example, various vitamins, minerals, breath-freshening agents, and therapeutic herbs can advantageously be incorporated into the articles. To maintain the efficacy of these agents, however, it is important to ensure that processing temperatures subsequent to the incorporation of the relevant agents do not exceed the degradation temperatures of the active component of the agents.

Collagen and/or gelatin derived materials are also very attractive for forming degradable/digestible chewing articles. These may be used as the primary ingredient in the article or they can be blended with starch-based materials. The resulting materials can be made to possess microbe-inhibiting properties by methods described herein.

A wide variety of comminuted vegetable matter can also be used as a primary ingredient for mastication articles or as a component ingredient in a blend (e.g., with starch, rawhide, gelatin, etc.).

Rope-Based Mastication Articles

Cotton is a highly absorbent material and is particularly attractive for constructing rope-based mastication articles; but when cotton becomes wet with saliva, it tends to dry relatively slowly, which can lead to bacteria growth.

A "passive" approach includes limiting bacterial proliferation by limiting the time for which the material is exposed to moisture, such as by the inclusion of a nonabsorbent core for a cotton covered rope chew article. But the article will frequently still be exposed to moisture for periods sufficiently long for significant bacterial proliferation to occur.

The present invention discloses an "active" and complete approach in which microbe-cidal agents are incorporated into the article. In this way, the article is directly protected against the proliferation of a wide variety of bacteria, as well as other microbes, regardless of factors such as the specific environment or the way the dog uses the article.

A preferred process for treating cotton rope-based mastication articles for pets, or for treating rope-based mastication articles for pets in which cotton is a major component, is to soak the rope material in a solution containing Ultra Fresh DM-50. It is generally desired to treat the rope in an aqueous solution so that the content of the agent in the rope is about 0.03%–1.2%, preferably between 0.08% and 0.6% by weight.

Another preferred method for treating cotton rope-based mastication articles for pets, or for treating rope-based mastication articles for pets in which cotton is a major component, is to soak the rope in a solution containing diiodomethyl-p-tolylsulphone. A preferred form of the agent is Ultrafresh UF-95, available from Thomas Research Associates. It is generally desired to treat the rope in an ethanol or acetone solution so that the final content of the agent in the rope is between 0.001% to 3%, preferably between 0.01% and 1%. Because this agent can cause yellowing in the final material, it may be desired to use color suppressants (especially if one is manufacturing a white rope).

Another preferred method for treating cotton rope-based mastication articles for pets, or for treating rope-based mastication articles for pets in which cotton is a major component, is to soak the rope in a solution containing Dow Corning 5700 strongly bonded microbe-inhibiting agent. Preferably, the agent content is in the range of about 0.08%–0.15% by weight.

Soak-treating in an aqueous solution containing stabilized chlorine dioxide (concentration range about 0.1–4%) is also preferred. Also preferred is triclosan. It is generally desired to soak the rope material in solution in which the concentration of triclosan is between 0.01% and 1.2%, preferably between 0.05% and 0.6% by weight. An alcohol, preferably ethanol, is the primary solvent of the preferred treatment solution.

The soaking (or spraying) solution can optionally contain ingredients that will impart a desirable scent or flavor to the articles. These ingredients include meat broth, meat meal, gravy, etc.

It is generally preferred to that the treatment occur at an elevated temperature, typically between 40–100° Celsius. If a temperature higher than the boiling temperature of the primary solvent is used, however, increased pressured must be used. For example, the articles can be treated in an aqueous solution at temperatures exceeding 100° C. if an autoclave or pressure cooker is used.

Adding an amount (typically 0.1–20% by weight) of a soluble or dispersable polymer or organic material to the treatment solution can assist in the retention of the microbe-inhibiting agent in the rope-material and is preferred. For example, one can incorporate many cellulose ether materials (e.g., methyl cellulose, hydroxyethyl cellulose, or carboxymethyl) or poly (vinyl alcohol) in water-based solvents. Starches, agar, gelatin, casein, lard, etc. can also be useful. Butyl cellulose is an example of a polymer which is soluble in ethanol, a preferred solvent for triclosan. Preferred microbe-inhibiting agents to be used with retention-assisting ingredients are triclosan, diiodomethyl-p-tolylsulphone, Ultra Fresh DM-50, and chlorine dioxide.

When using retention aids, the solvent, retention aid and the microbe-inhibiting agent should be selected so that both the retention aid and the microbe-inhibiting agent are sufficiently soluble or dispersable in the solvent.

Many desired retention aids are easily digestible by microbes, and it is therefore desirable that the microbe-inhibiting agents are present in the retention aids at concentrations sufficient to inhibit the proliferation of microbes.

The rope material can also be disinfected or sanitized prior to its treatment by soaking in a disinfecting solution (e.g., ethanol), optionally at elevated temperature or pressure. The rope materials can also be sprayed with the treatment solutions.

After a soak or spray treatment, the rope material is dried. Air-drying and oven drying are preferred, as is drying in a vacuum oven, optionally at elevated temperature.

Another preferred method for constructing a microbe-inhibiting cotton-rope-based mastication article is to spray with or otherwise expose the individual filaments or threads to the microbe-inhibiting agent (either in solution or carrier form) as the rope is being formed. In order to expand the threads and make them more open to the introduction of the microbe-inhibiting agents, it is preferable to expose the threads to moisture before the microbe-inhibiting agents are introduced. The microbe inhibiting agents may be introduced by spraying a solution containing the agent (solutions with concentrations similar to that of the soak-treatment solutions can be used) onto the filaments. The agents can be dissolved in solution or can be part of a dispersion.

Other natural materials are useful in constructing rope-based mastication articles for pets. These include sisal, hemp, jute, henequen, and others. Ultra Fresh DM-50, diiodomethyl-p-tolylsulphone, Dow 5700, chlorine dioxide and triclosan are the preferred agents for treating these materials.

Rope-based mastication articles can be made from a variety of synthetic materials as well. They can be constructed, e.g., from fibers or threads composed of nylon, orlon or other acrylics, polyester, polypropylene, or other materials. For these materials, it is preferred to incorporate triclosan (e.g., Microban, Irgasan, Ultrafresh NM-100) or diiodomethyl-p-tolylsulphone (e.g., Ultrafresh UF-95) at the time of manufacture of the raw filaments. The agent is preferably incorporated into the melt or spin dope from which the filaments are drawn. For triclosan, it is preferred that the concentration in the finished filaments be between 0.01% and 1.8%, preferably between 0.05% and 1% by weight. For UF-95, it is preferred that the concentration in the finished filaments be between 0.001% to 3%, preferably between 0.01% and 1%.

A rope can be combined with other functional features to create an improved mastication article. For example, holes can be punched through microbe-inhibiting rawhide articles according to the invention and a microbe-inhibiting rope according to the invention can be threaded through the holes. The rope can then be knotted at either end to secure the rawhide to the rope. Similarly, a microbe-inhibiting rope according to the invention can be threaded through a fiber-filled plush chew toy for a pet and triclosan microbe-inhibiting agent can be incorporated in all or part of the fiber in the plush chew toy.

Plastic Mastication Articles

Plastic-based mastication articles for pets are becoming increasingly popular. Except in some cases where degradable polymers are used, plastic-based mastication articles are not intended for digestion. Many non-digestible plastics possess a moderate natural microbe-starving quality—they provide little or no nutritive material for microbes to digest or metabolize and thereby thrive. Even with these articles, however, saliva and other fluids or materials deposit on the articles and provide nutrition for the proliferation of microbes. In addition, many plasticizers which are often used to increase flexibility in the final plastic article or to facilitate processing are readily digestible by microbes as described further below.

A greater source of nutrition in plastic-based mastication articles for pets relates to the methods by which the articles are made desirable to pets. Plastics are generally not particularly attractive to pets, especially those plastics that possess good natural microbe-starving characteristics. For this reason, animal meal, sugar, and similar attractive elements have been incorporated into such plastic-based mastication articles to make them more attractive for pets. Because these elements are also digestible by microbes, however, the natural microbe-starving characteristics which the articles may have possessed can become ineffectual.

According to one aspect of the invention, plastic-based mastication articles possess effective protection against the proliferation of microbes, even when digestible elements intended to make the articles more attractive for pets have been incorporated into the articles.

Plastic mastication articles for pets are frequently made by molding (e.g., injection molding, blow molding), or dipping processes known in the plastics fabrication art. Thermoplastic resins are typically used for injection molding and latex solutions are typically used for the dipping processes.

For articles constructed by molding processes, it is preferred first to incorporate the agent in a concentrated form into a resin carrier. U.S. Pat. No. 4,789,692, which is herein incorporated by reference, discloses numerous means for concentrating biocides in resin carriers. The resin carrier is then mixed or diluted in the appropriate ratio with the resin(s) with which it will comprise the final article, and the blend is processed, preferably by injection molding, into the desired shape. It is crucial to ensure that the resin mix is well-blended. The mixing or dilution factor is given by the ratio of the concentration of the agent in the concentrate to the desired final concentration in the article. For example, if the concentrated carrier contained 2% of the agent, and the desired final concentration was 0.2%, the mixing or dilution factor would be 2%/0.2%=10, e.g., the final mix would contain 1 part in 10 of the concentrated carrier.

Diiodomethyl-p-tolylsulphone is a preferred agent. It is preferred to incorporate UF-95 into the concentrated resin fraction such that the concentration in the final article is between 0.001% to 3%, preferably between 0.01% and 1%. The preferred concentration of UF-95 in the concentrated resin depends on the polymer or polymers comprising the resin, but is generally between 0.5% and 15%, preferably between 1% and 9%.

Preferred plastic materials for the articles according to the invention, alone or in combination, are nylon and polyurethane, although many other types of plastics, e.g., polyolefins, are suitable as well. It is generally preferred to use thermoplastics.

Another preferred microbe-inhibiting agent is 2,4,4'-trichloro-2'-hydroxydiphenol (triclosan). The microbe-inhibiting resin fraction is added to the base material resin in an amount such that the concentration of the agent in the final product is between 0.001% and 1.5%, preferably between 0.004% and 0.7% by weight. The preferred concentration of triclosan in the concentrated resin depends on the polymer or polymers comprising the resin, but is generally between 0.5% and 15%, preferably between 1% and 9%.

Another preferred agent is a form of triclosan commercially available as Ultra Fresh NM-100. It is added such that its concentration in the final article is between 0.001% and 1.5%, preferably between 0.004% and 0.7% by weight.

In latex processing, the microbe-inhibiting agent is in powder or liquid form or suitably and is incorporated into a solid or liquid carrier that is preferably added to the latex mixture before molding. Preferred microbe-inhibiting agents are triclosan, diiodomethyl-p-tolylsulphone, tri-n-butylin maleate, and chlorine dioxide.

2,4,4'-trichloro-2'-hydroxydiphenol can also be obtained in a crystalline powder form (e.g., from TRInternational, Inc.), and the powder can be added to the article forming composition. For example, the powder can be added directly to the latex mixture. It can also be incorporated directly into the molten form of many thermoplastics. In the latter case, however, appropriate mixing should be carried out to ensure homogeneity.

Other desirable ingredients, such as meat broths, ground-up dried meat products, etc., can be added to the plastic-based mastication articles to impart a desirable flavor or scent. The addition of such ingredients can, however, negate the natural microbe-starving quality of these base polymer materials. Unfortunately, ingredients which are likely to make the make the article more attractive to pets are generally of a digestible nature (meat-based products, sugars, etc.), and are therefore likely to provide nutrition for the proliferation of microbes. This fundamental trade-off is circumvented by the invention. According to the invention, plastics-based mastication articles with such flavoring ingredients include a microbe-inhibiting agent in the resin mix or the precursor solution of the base plastic material. The preferred concentrations and related considerations given above apply.

A preferred method for constructing plastics-based mastication articles with such flavoring ingredients is to pre-treat the flavoring ingredients themselves with microbe-inhibiting agents. These pre-treatments can be done alone or in combination with adding microbe-inhibiting agent to the base plastic material.

If one is incorporating a solid or solid-like flavoring ingredient into a resin or melt mixture, it is preferred to soak the flavoring ingredients in a solution containing one or more microbe-inhibiting agents before incorporating the ingredients intro the resin or melt mixture. The ingredients should be dried before incorporation into the resin or melt mixture.

A preferred agent for use in treating the flavoring ingredients is chlorine dioxide, which is safe for both animal and human consumption. An appropriate solution concentration is in the range of about 0.1–2% by weight.

Also preferred is diiodomethyl-p-tolylsulphone. The treatment solution has a concentration between 0.01% and 5%, preferably between 0.05% and 2% by weight. Ethanol or acetone are preferred candidates for the primary solvent of the treatment solution. When treating by soaking in a diiodomethyl-p-tolylsulphone solution, subsequent rinsing in an aqueous solution is preferred.

Also preferred is Ultrafresh DM-50. Water is the primary solvent for the preferred treatment solution, which contains between 0.005%–0.4%, preferably 0.008%–0.1% by weight, of the DM-50 agent.

Also preferred is triclosan. The treatment solution has a concentration between 0.01% and 1.2%, preferably between 0.05% and 0.6% by weight. An alcohol, preferably ethanol, is the primary solvent of the preferred treatment solution. When treating by soaking in a triclosan solution, subsequent rinsing in an aqueous solution is preferred.

If one is incorporating a flavoring agent by soaking the article in a solution containing that agent (and possibly at elevated temperature and/or pressure), it is preferred to incorporate a preferred microbe-inhibiting agent in the treatment solution. A preferred agent in this case is chlorine dioxide, preferably in the range of about 0.1–2% by weight.

The microbe-starving quality of some synthetic polymers is often unintentionally destroyed by processing with a plasticizer which contains nutritive elements which can support microbial proliferation. The plasticizers used in processing many polymers are digestible and/or degradable by microbes. If a plasticizer is to be used in processing materials used for constructing a mastication article for a pet, it is preferred to choose a plasticizer that does not diminish the natural microbe-starving and/or microbe-impenetrable property of the polymer. Plasticizers that are particularly resistant to fungal growth include: Abietic acid; hydrog. methyl abietate; tri-n-butyl aconitate; triethyl aconitate; di-(2-ethylhexyl)adipate; di-(2-ethylhexyl)acetate; ethyl-o-benzyl benzoate; chlorinated diphenyls; chlorinated paraffins; tri-n-butyl citrate; triethyl citrate; 2-nitro-2 methyl-1,3-propanediol diacetate; dimethyl phthalate; di-n-propyl phthalate; diisopropyl phthalate; dibutyl phthalate; diisobutyl phthalate; diisodecyl phthalate; dihexyl phthalate; dicapryl phthalate; di-(2 ethylhexel) phthalate; di-(2 ethylhexyl) phthalate; dicyclohexyl phthalate; dicyclohexyl phthalate; and dibenzyl phthalate.

Other Types of Plastic Articles

Plastics articles to be used for purposes other than as mastication articles for pets can be made with a microbe-inhibiting agent according to the invention. Particularly desirable are feeding bowls, litter boxes, and scoopers (e.g., for food, feces, used litter). It is preferred first to incorporate the microbe inhibiting agent in a concentrated form into a resin carrier. U.S. Pat. No. 4,789,692, which is herein incorporated by reference, discloses numerous techniques for concentrating biocides in resin carriers. The resin carrier is then mixed or diluted in an appropriate ratio with the resin(s) which will be used in the final article, and the blend is processed, preferably by injection molding, into the desired shape. The mixing or dilution factor is given by the ratio of the concentration by weight of the microbe-inhibiting agent in the resin carrier to the desired final concentration by weight in the article. For example, if the concentrated carrier contained 2% of the microbe-inhibiting agent by weight, and the desired final concentration was 0.2% by weight, the mixing or dilution factor would be 2%/0.2%=10, e.g., the final mix would contain 1 part in 10 of the concentrated carrier.

For bowls or other food-contacting products, diiodomethyl-p-tolylsulphone is the preferred microbe-inhibiting agent. It is specifically preferred to incorporate UF-95 into the concentrated resin fraction such that the concentration in the final article is between 0.001% to 3%, preferably between 0.01% and 0.1%. The preferred concentration of UF-95 in the concentrated resin depends on the polymer or polymers comprising the resin, but is generally between 0.5% and 15%, preferably between 1% and 9%.

The primary material comprising the bowl is preferably polypropylene, polyethylene, although many thermoplastic polymers are adequate.

Triclosan is also preferred for bowls in cases where anti-mildew and anti-mold properties are not essential. Using triclosan, it is preferred to incorporate the agent into a resin concentrate which is then blended with other resin to produce the final article via injection molding. It is preferred to incorporate UF-95 into the concentrated resin fraction such that the concentration in the final article is between 0.001% to 3%, preferably between 0.01% and 1%. The preferred concentration of triclosan in the concentrated resin depends on the polymer or polymers comprising the resin, but is generally between 0.5% and 15%, preferably between 1% and 9%.

For litter boxes and scoopers which will contact feces or other bodily waste, tri-n-butylin maleate is the preferred microbe-inhibiting agent. A commercial form, Ultrafresh DM-50, is specifically preferred. It is preferred to incorporate DM-50 into the concentrated resin fraction such that the concentration in the final article is between 0.005% to 4% by weight, preferably between 0.04% and 2%. The preferred concentration of DM-50 in the concentrated resin depends on the polymer or polymers in the resin blend, but is generally between 0.5% and 15%, preferably between 1% and 9% by weight.

Diiodomethyl-p-tolylsulphone is also a preferred microbe-inhibiting agent. It is preferred to incorporate UF-95 into the concentrated resin fraction such that the concentration in the final article is between 0.005% to 4%, preferably between 0.05% and 2%. By weight The preferred concentration of UF-95 in the concentrated resin depends on the polymer or polymers comprising the resin, but is generally between 0.5% and 15%, preferably between 1% and 9% by weight.

Combs and other grooming aids can similarly be manufactured according to the invention.

Mastication Articles with Porosity

It is sometimes desirable, especially for animals that do not have powerful jaws (such as small dogs, cats, and rodents), to have a substantial porosity in the mastication articles according to the invention. In such cases, the articles can be made porous with well-known foaming techniques as disclosed, for example, in U.S. Pat. No. 5,360,830, which is herein incorporated by reference.

The following examples illustrate specific embodiments of the invention:

EXAMPLE 1

A treatment bath was prepared as follows: A chlorine dioxide starting solution comprising 2% by weight chlorine dioxide and 0.085% by weight sodium carbonate was obtained (from 3R Marketing Associates). 100 ml of this solution was mixed with 400 ml of water. The solution was heated to 90 C. Four grams of agar was then added to this solution.

Rawhide was acquired commercially in strip form. A strip with dimensions approximately 6 cm×6 cm, and about 1.6 mm thick was cut using a knife.

The rawhide strip was placed in the treatment bath, which was then covered. The strip was treated in the bath, with occasional stirring, for 2 hours.

The strip was removed from the bath and air dried.

EXAMPLE 2

A first treatment bath is prepared using 800 ml of water as the treatment solution.

A second treatment bath was prepared as follows: A mixture of 1 gm of triclosan crystalline powder (obtained from TRInternational, Inc.) was mixed with 200 ml of grain alcohol (95% ethanol by volume); and the mixture was stirred.

A third treatment bath is prepared using 800 ml of water maintained at 80° C.

Rawhide was acquired commercially in strip form. A strip with dimensions approximately 6 cm×6 cm, and about 1.6 mm thick was cut using a knife.

The rawhide strip was placed in the first treatment bath, which was then covered. The bath with the strip was allowed to sit at room temperature for eight hours The rawhide strip was then removed from the first treatment bath and placed into the second treatment bath, which was then covered. The bath with the strip was maintained, with occasional stirring, at room temperature for four hours.

The rawhide strip was then removed from the second treatment bath and placed into the third treatment bath, which was then covered. The third treatment bath with the strip was allowed to sit at 80° C. for four hours.

The strip was removed from the bath and air dried.

EXAMPLE 3

A first treatment bath is prepared using 800 ml of a 0.9% saline solution (0.9% by weight Sodium Chloride Irrigation, USP, from Baxter Healthcare Corporation).

A second treatment bath was prepared as follows: A mixture of 0.3 gm of triclosan crystalline powder (obtained from TRInternational, Inc.) was mixed with 200 ml of grain alcohol (95% ethanol by volume); and the mixture was stirred.

Rawhide was acquired commercially in strip form. A strip with dimensions approximately 6 cm×6 cm, and about 1.6 mm thick was cut using a knife.

The rawhide strip was placed in the first treatment bath at room temperature and then covered for six hours. The rawhide strip was then removed from the first treatment bath and rinsed with water. It was then placed into the second treatment bath, which was then covered, and soaked at room temperature for three hours. The strip was then removed from the bath, rinsed generously with water and air dried.

EXAMPLE 4

A treatment bath was prepared as follows: A mixture of 0.7 gm of triclosan crystalline powder (obtained from TRInternational, Inc.) was mixed with 100 ml of grain alcohol (95% ethanol by volume); and the mixture was stirred. 100 ml of water was added to the mixture, causing the solution to take on a white, milky appearance.

Rawhide was acquired commercially in strip form. A strip with dimensions approximately 6 cm×6 cm, and about 1.6 mm thick was cut using a knife.

The rawhide strip was placed in the treatment bath, which was then covered, and soaked at room temperature for eight hours. The strip was then removed from the bath and air dried.

EXAMPLE 5

A first treatment bath is prepared by adding two ounces of sugar to 800 ml of water, and stirring and heating until the sugar dissolves. The bath is then placed on a hotplate and maintained at 60° C.

A second treatment bath was prepared as follows: A solution of 0.3% by weight Ultra Fresh DM-50 in water (Thomas Research Associates) is covered and heated at 35° C.

Rawhide was acquired commercially in strip form. A strip with dimensions approximately 6 cm×6 cm, and about 1.6 mm thick was cut using a knife.

The rawhide strip was placed in the first treatment bath, which was then covered. The bath with the strip was allowed to sit at 60° C. for 3 hours.

The rawhide strip was removed from the first treatment bath, rinsed generously, and placed into the second treatment bath, which was then covered. The bath with the strip was allowed to sit at 35° C. for four hours.

The strip was removed from the bath and dried in an oven for 1 hour at 85° C.

EXAMPLE 6

An 8" length piece is cut from a roll of cotton rope. An aqueous treatment solution is prepared containing 0.2% by weight Ultra Fresh DM-50 (Thomas Research Associates). The solution is kept covered and maintained at room temperature. The cut rope is placed into the treatment solution, weighted down with a U-shaped piece of glass. The rope piece is periodically agitated in the treatment solution. After 2 hours, the rope is removed from the treatment solution and dried in a vacuum oven at 60° C.

EXAMPLE 7

An 10" length piece is cut from a roll of cotton rope. A treatment solution is prepared comprising an ethanol solvent with 0.2% by weight triclosan (obtained from TRInternational, Inc.) and 1% by weight butyl cellulose. The solution is heated to 40° C. and kept covered. The cut rope is rope is placed into the treatment solution and is periodically agitated. After 1.2 hours, the rope is removed from the treatment solution and hung from a clothesline for 40 minutes. The rope is then dried in a vacuum oven at 80° C.

EXAMPLE 8

An 8" length piece is cut from a roll of cotton rope. A knot is tied at either end to give the rope the appearance roughly of a bone. An aqueous treatment solution is prepared as follows: 300 ml of a chlorine dioxide starting solution comprising 2% by weight chlorine dioxide and 0.085% by weight sodium carbonate (from 3R Marketing Associates) was mixed with 700 ml of water. The solution is maintained at 80° C. 20 gm of beef flavor bouillon (Herbox, from Hormel Foods) is added to the solution, which is stirred until the bouillon is dissolved. The solution is kept covered and maintained at 80° C. The cut rope is rope is placed into the treatment solution and weighted down with a U-shaped piece of glass. The rope piece is periodically agitated in the treatment solution. After 2 hours, the rope is removed from the treatment solution and dried in a vacuum oven at 60° C.

EXAMPLE 9

An 8" length piece is cut from a roll of cotton rope. A knot is tied at either end to give the rope the appearance roughly of a bone. An aqueous treatment solution is prepared as follows: 300 ml of a chlorine dioxide starting solution comprising 2% by weight chlorine dioxide and 0.085% by weight sodium carbonate (from 3R Marketing Associates) is mixed with 700 ml of water. The solution is heated to and maintained at 95° C. 10 gm of agar is stirred into the solution. The cut rope is rope is placed into the treatment solution and weighted down with a U-shaped piece of glass. The rope piece is periodically agitated in the treatment solution. After 2 hours, the rope is removed from the treatment solution and dried in a vacuum oven at 60° C.

EXAMPLE 10

98 gm of dry starch are mixed 38 gm of maleated ethylene-propylene copolymer. This mixture is then blended with 4 gm of a carrier resin comprising 7% Ultrafresh UF-95 in ethylene vinyl acetate. This mixture is then mixed in an internal hot mixer for 12 minutes at 185° C. The resulting material can be used as raw material for molding a mastication article.

EXAMPLE 11

9.8 kg of dry starch are mixed with 3.8 kg of maleated ethylene-propylene copolymer. This material is mixed in an internal hot mixer for 12 minutes at 185° C. The resulting material is then extruded into pellet form. The resulting pellets are blended with 400 gm of a carrier resin pellets comprising 6% Ultrafresh UF-95 in ethylene vinyl acetate. Care is taken to ensure that the sizes of the pellets are comparable. The blend is placed in the hopper of an injection molding machine and is used for injecting molding a bone-shaped chewing article for a dog.

EXAMPLE 12

Ultrafresh UF-95 is incorporated at a concentration 2% by weight into an ethylene vinyl acetate carrier resin which is processed to be in pellet form. 20 gm of this material is mixed with 110 gm of a dry starch powder and 80 grams of polypropylene. This mixture is then mixed in an internal hot mixer for 12 minutes at 185° C. The resulting material can be used as raw material for molding a mastication article.

EXAMPLE 13

14 kg polypropylene pellets are blended with 400 gm of a carrier resin pellets comprising 3% Ultrafresh UF-95 in ethylene vinyl acetate. Care is taken to ensure that the sizes of the pellets are comparable. The blend is placed in the hopper of an injection molding machine and is used for injecting molding a feeding bowl for a dog.

EXAMPLE 14

Polypropylene resin in pellet form and ethylene vinyl acetate in pellet form containing 6% Ultrafresh UF-95 are separately fed into the feeders of a dual-feed injection molding machine at a proportion of 40 parts polypropylene to 1 part ethylene vinyl acetate. The material is injection molded into the shape of a feeding bowl for dogs.

EXAMPLE 15

Polypropylene resin in pellet form and polypropylene resin in pellet form containing 3% triclosan by weight are separately fed into the feeders of a dual-feed injection molding machine at a proportion of 35 parts polypropylene to 1 part treated polypropylene by weight. The material is injection molded into the shape of a bone shaped mastication article.

Reasonable variation and modification are possible within the forgoing disclosure and drawings without departing from the spirit of the invention which is defined in the appended claims.

What is claimed is:

1. A mastication article constructed for mastication by a domestic animal comprising:
    a touch chew-resistant material defining a shape in the form of a small article for enticing or being retrieved by a domestic animal;
    the chew-resistant material having bound therein an effective amount of a microbe-inhibiting agent in a durable, microbe-inhibiting agent retention system in which the microbe-inhibiting agent does not readily dissolve under ambient conditions in aqueous liquids with which the system comes into contact to prevent proliferation of microbes in and on the chew resistant material, the microbe-inhibiting agent further being present in an amount that is non-toxic, non-carcinogenic, and effectively non-allergenic at the levels used in the article.

2. A mastication article according to claim 1 wherein the microbe-inhibiting agent is selected from the group consisting of diiodomethyl-p-tolylsulphone, tri-n-butyltin maleate and triclosan.

3. A mastication article according to claim 1 wherein the microbe-inhibiting agent is diiodomethyl-p-tolylsulphone.

4. A mastication article according to claim 1 wherein the microbe-inhibiting agent is in particulate form and is coated onto core particles in the chew-resistant material to form an active layer, and the active layer includes a barrier coating which controls the rate of release of the microbe-inhibiting agent.

5. A mastication article according to claim 1 wherein the microbe-inhibiting agent is in particulate form and is coated onto core particles in the chew-resistant material to form an active layer, and the active layer includes a dispersion coating, whereby the core particles in the material are dispersed.

6. A mastication article according to claim 1 wherein the chew-resistant material is selected from the group consisting of nylon, polyurethane, polyolefins and blends thereof.

7. A mastication article according to claim 6 wherein the microbe-inhibiting agent is 2,4,4'-trichloro-2'-hydroxydiphenol.

8. A mastication article according to claim 6 wherein the 2,4,4'-trichloro-2'-hydroxydiphenol is present from 0.001 to 1.5 percent by weight of the mastication article.

9. A mastication article according to claim 6 wherein the microbe-inhibiting agent is tri-n-butylin maleate.

10. A mastication article according to claim 9 wherein the tri-n-butylin maleate is present from 0.001 to 1 percent by weight of the mastication article.

11. A mastication article according to claim 6 wherein the microbe-inhibiting agent is chlorine dioxide.

12. A mastication article according to claim 6 wherein the chew-resistant material includes a nutritive attracting agent.

13. A mastication article according to claim 12 wherein the nutritive attracting agent is selected from the group consisting of animal meal, meat broth, dried meat, sugar and blends thereof.

14. A mastication article according to claim 6 wherein the microbe-inhibiting agent or property is chlorine dioxide.

15. A mastication article according to claim 1 wherein the microbe-inhibiting agent is selected from the group consisting of diiodomethyl-p-tolylsulphone, tri-n-butyltin maleate and triclosan.

16. A mastication article according to claim 1 wherein the microbe-inhibiting agent is diiodomethyl-p-tolylsulphone.

17. A mastication article according to claim 1 wherein the chew-resistant material is made from the group consisting of animal skin, animal fat, vegetable, or a blend thereof.

18. A mastication article according to claim 1 wherein the material is selected from a group consisting of polymeric resins or latex compositions, fibers or threads, textile materials, foams, or blends thereof.

19. A mastication article according to claim 1 wherein the microbe-inhibiting agent is 2,4,4'-trichloro-2'-hydroxydiphenol.

20. A mastication article according to claim 1 wherein the microbe-inhibiting agent is tri-n-butylin maleate.

21. A mastication article according to claim 1 wherein the microbe-inhibiting agent is chlorine dioxide or triclosan.

22. A mastication article according to claim 1 wherein the microbe-inhibiting agent is 3-trimethoxysilylpropyldimethyloctadecyl ammonium chloride.

23. A mastication article according to claim 1 wherein the microbe-inhibiting agent is a complex of polysubstituted imine salts and trialkyl phosphate esters with free alkylated phosphoric acid.

24. A mastication article according to claim 1 wherein the microbe-inhibiting agent is in particulate form and is coated onto core particles in the chew-resistant material to form an active layer.

25. A mastication article according to claim 24 wherein the core particles are selected from a group comprising zinc oxide, titanium oxide, barium sulfate, or a blend thereof.

26. A mastication article according to claim 24 wherein the active layer is selected from a group comprising silver, copper oxide, zinc silicate, or a blend thereof.

27. A mastication article according to claim 1 wherein the tough chew-resistant material is digestible or otherwise degradable.

28. A mastication article according to claim 27 wherein the digestible material is rawhide.

29. A mastication article according to claim 27 wherein the digestible material is selected from the group consisting of animal skin, animal fat, vegetable, corn starch, potato starch and blends thereof.

30. A mastication article according to claim 1 wherein the tough chew-resistant material includes rope.

31. A mastication article according to claim 3 wherein the rope comprises a material selected from the group consisting of cotton, sisal, hemp, jute, henequen and blends thereof.

32. A mastication article according to claim 31 wherein the microbe-inhibiting agent is tri-n-butylin maleate.

33. A mastication article according to claim 32 wherein the tri-n-butylin maleate is present from 0.03 to 1.2 percent by weight of the mastication article.

34. A mastication article according to claim 31 wherein the tri-n-butylin maleate is 3-trimethoxysilylpropyldimethyloctadecyl ammonium chloride.

35. A mastication article according to claim 34 wherein the 3-trimethoxysilylpropyldimethyloctadecyl ammonium chloride is present from 0.08 to 0.15 percent by weight of the mastication article.

36. A mastication article according to claim 31 wherein the microbe-inhibiting agent is chlorine dioxide.

37. A mastication article according to claim 36 wherein the chlorine dioxide is present from 0.01 to 1.2 percent by weight of the mastication article.

38. A mastication article according to claim 31 wherein the microbe-inhibiting agent is 2,4,4'-trichloro-2'-hydroxydiphenol.

39. A mastication article according to claim 30 wherein the rope is selected from the group consisting of nylon, acrylic, polyester, polypropylene and blends thereof.

40. A mastication article according to claim 39 wherein the microbe-inhibiting agent is 2,4,4'-trichloro-2'-hydroxydiphenol.

41. A mastication article according to claim 40 wherein the 2,4,4'-trichloro-2'-hydroxydiphenol is present from 0.01 to 1.8 percent by weight of the mastication article.

42. A mastication article according to claim 1 wherein the article is formed by molding the tough chew resistant material into a geometric shape.

43. A mastication article according to claim 1 wherein the tough chew resistant material is sufficiently dense and slow to absorb water that it retains its mechanical integrity and chewability for a significant period of time before it becomes soft.

44. A mastication article according to claim 1 wherein the tough chew resistant material further includes a plasticizing material.

45. A mastication article according to claim 44 wherein the plasticizing material is at least one component selected from the group consisting of poly-ethylene-acrylic acid, poly-ethylene-vinyl alcohol, polyethylene, polypropylene, polystyrene, polyvinyl chloride, polyurethane, polyester, polyamide, polyacrylate, polyether, polyisoprene, rubbers, and polylactide, sorbitol, glycerol, sucrose, water and fructose.

46. A mastication article according to claim 45 wherein the plasticizer is present in the tough chew resistant material in an amount ranging from 1% to 20% by weight.

47. A mastication article according to claim 44 wherein the microbe-inhibiting agent is incorporated into the plasticizing material.

48. A mastication article according to claim 1 wherein the starch is corn starch.

49. A mastication article according to claim 1 wherein the microbe-inhibiting agent is present in the chew-resistant material in an amount between 0.001% to 3% by weight.

50. A mastication article according to claim 1 wherein the microbe-inhibiting agent is present in the chew-resistant material in an amount between 0.01% to 1% by weight.

51. A mastication article according to claim 1 and further including an animal enticing agent.

52. A mastication article according to claim 51 wherein the enticing agent is selected from the group consisting of catnip, catnip oil, fish scent, and meat scents.

53. A mastication article according to claim 1 wherein the chew-resistant material further includes at least one of collagen and gelatin derived materials.

54. A plastic article for a domestic animal wherein the article is formed by molding a chew resistant synthetic resin into a geometric shape;

the synthetic resin having an effective amount of a microbe-inhibiting agent bound therein in a durable, microbe-inhibiting agent retention system in which the microbe-inhibiting agent does not readily dissolve under ambient conditions in aqueous liquids with which the system comes into contact to prevent proliferation of microbes in and on the chew resistant synthetic resin, the microbe-inhibiting agent further being present in an amount that is non-toxic, non-carcinogenic, and effectively non-allergenic at the levels used in the article.

55. A plastic article according to claim 54 wherein the synthetic resin is non-digestible and selected from the group consisting of polymeric resins and latex compositions.

56. A plastic article according to claim 54 wherein the microbe-inhibiting agent is 2,4,4'-trichloro-2'-hydroxydiphenol.

57. A plastic article according to claim 54 wherein the microbe-inhibiting agent is tri-n-butylin maleate.

58. A plastic article according to claim 54 wherein the microbe-inhibiting agent is chlorine dioxide.

59. A plastic article according to claim 54 wherein the microbe-inhibiting agent is 3-trimethoxysilylpropyldimethyloctadecyl ammonium chloride.

60. A plastic article according to claim 54 wherein the microbe-inhibiting agent is a complex of polysubstituted imine salts and trialkyl phosphate esters with free alkylated phosphoric acid.

61. A plastic article according to claim 54 wherein the microbe-inhibiting agent is in particulate form and is coated onto core particles incorporated into the synthetic resin.

62. A plastic article according to claim 61 wherein the core particles are selected from a group comprising zinc oxide, titanium oxide, barium sulfate, or a blend thereof.

63. A plastic article according to claim 62 wherein the core particles have an active layer selected from the group consisting of silver, copper oxide, zinc silicate and blends thereof.

64. A plastic article according to claim 63 wherein the active layer further includes a barrier coating which controls the rate of release of the microbe-inhibiting agent.

65. A plastic article according to claim 63 wherein the active layer further includes a dispersion coating which assists in the dispersion of the core particles in the resin.

66. A plastic article according to claim 54 wherein the geometric shape is a bowl for containing pet food or drink.

67. A plastic article according to claim 66 wherein the material is a polymer and the microbe-inhibiting agent is 2,4,4'-trichloro-2'-hydroxydiphenol.

68. A plastic article according to claim 67 wherein the microbe-inhibiting agent is present from about 0.0005 to 1.2 percent by weight of the plastic article.

69. A process for reducing the growth of microbes in a mastication article having a tough, chew-resistant material and defining a shape in the form of a small article for enticing or being retrieved by a domestic animal, comprising the step of binding in the chew-resistant material an effective amount of a microbe-inhibiting agent in a durable, microbe-inhibiting agent retention system in which the microbe-inhibiting agent does not readily dissolve under ambient conditions in aqueous liquids with which the system comes into contact to prevent proliferation of microbes in and on the chew resistant material, the microbe-inhibiting agent further being present in an amount that is non-toxic, non-carcinogenic, and effectively non-allergenic at the levels used in the article.

70. A process according to claim 69 wherein the application step includes applying or incorporating a solution including the microbe-inhibiting agent to the chew-resistant material.

71. A process according to claim 70 wherein the application step includes soaking the chew-resistant material in the solution including the microbe-inhibiting agent.

72. A process according to claim 70 wherein the application step includes spraying the chew-resistant material with the solution including the microbe-inhibiting agent.

73. A process according to claim 69 wherein the application step includes coating particles with the microbe-inhibiting agent, and the coated particles are incorporated into the core of the chew-resistant material.

74. A process according to claim 69 wherein the chew-resistant material includes fibers and the application step includes incorporating the microbe-inhibiting agent into a dope before spinning the fibers.

75. A process according to claim 69 wherein the application step includes incorporating the microbe inhibiting agent into a spray for coating the chew resistant material.

76. A process according to claim 69 wherein the chew resistant material is rawhide and further comprising the step of cleaning the rawhide and the application step includes applying the microbe-inhibiting agent to or incorporating into the microbe-inhibiting agent into the rawhide during rawhide cleaning step.

77. A process according to claim 69 wherein the chew-resistant material is rawhide and further comprising the step of liming the rawhide and the application step includes applying the microbe-inhibiting agent to or incorporating into the microbe-inhibiting agent into the rawhide during rawhide liming step.

78. A process according to claim 69 and further comprising the step of spraying the chew-resistant material with a solution which includes an attracting agent which will impart a flavor or a smell to the chew-resistant material.

79. A process according to claim 69 wherein the application step includes applying the microbe-inhibiting agent at a temperature between 40 and 100 degrees Celsius.

80. A process according to claim 69 wherein the chew-resistant material includes cotton-containing rope and wherein the application step includes applying moisture to the cotton rope, and then spraying the cotton-containing rope with a solution including the microbe-inhibiting agent.

81. A process according to claim 69 wherein the chew-resistant material includes fibers and the applying or incorporating step includes adding the microbe-inhibiting agent to a dope for spinning a portion of the fibers.

82. A process according to claim 69 wherein the step of incorporating a microbe-inhibiting agent includes adding the microbe-inhibiting agent to a synthetic resin and further comprising the step of molding the synthetic resin into the chew-resistant material.

83. A process according to claim 82 wherein the step of adding the microbe-inhibiting agent to a synthetic resin comprises incorporating the microbe-inhibiting agent into a carrier material that is compatible with the synthetic resin and blending the carrier material with the synthetic resin prior to the molding step.

84. A process according to claim 83 wherein the carrier material is the same as the synthetic resin.

85. A process according to claim 82 wherein the synthetic resin includes an attracting agent which will impart a flavor or a smell to the mastication article.

86. A process according to claim 69 wherein the step of incorporating a microbe-inhibiting agent includes adding the microbe-inhibiting agent to a latex mixture, and further comprising the step of molding the chew-resistant material.

87. A process according to claim 69 wherein the material is digestable and the step of incorporating a microbe-inhibiting agent includes adding the microbe-inhibiting agent to the chew-resistant material when the chew-resistant material is in a molten or substantially liquid state, and further comprising the step of molding the chew-resistant material to form the article.

88. A process according to claim 69 wherein the step of incorporating a microbe-inhibiting agent includes the step of applying a solution including the microbe-inhibiting agent to the material.

89. A process according to claim 88 wherein the step of incorporating a microbe-inhibiting agent includes the step of applying the solution including the microbe-inhibiting agent to the chew-resistant material after it has been formed.

90. A process according to claim 88 wherein the step of incorporating a microbe-inhibiting agent includes soaking the chew-resistant material in the solution before the chew-resistant article has been formed.

91. A process according to claim 88 wherein the microbe-inhibiting agent is selected from a group consisting of triclosan, chlorine dioxide, diiodomethyl-p-tolylsulphone, tri-n-butyltin maleate, garlic and turmeric.

92. A process according to claim 69 wherein the microbe-inhibiting agent is chlorine dioxide or triclosan.

93. A process according to claim 69 wherein the microbe-inhibiting agent is 2,4,4'-trichloro-2'-hydroxydiphenol.

94. A process according to claim 69 wherein the microbe-inhibiting agent is tri-n-butylin maleate.

* * * * *

UNITED STATES PATENT AND TRADEMARK OFFICE
CERTIFICATE OF CORRECTION

PATENT NO. : 6,178,922 B1
DATED : January 30, 2001
INVENTOR(S) : Denesuk et al.

It is certified that error appears in the above-identified patent and that said Letters Patent is hereby corrected as shown below:

Title page,
Item [54], The title should read -- MASTICATION ARTICLES POSSESSING MICROBE-INHIBITING PROPERTIES --.

Column 25,
Line 25, "touch" should read -- tough --
Line 67, "tri-n-butylin maleate" should read -- tri-n-butyltin maleate --

Column 26,
Lines 31 and 67, "tri-n-butylin maleate" should read -- tri-n-butyltin maleate --
Line 63, "3" should read -- 30 --.

Column 27,
Line 2, "tri-n-butylin maleate" should read -- tri-n-butyltin maleate --

Column 28,
Line 22, "tri-n-butylin maleate" should read -- tri-n-butyltin maleate --

Column 30,
Line 50, "tri-n-butylin maleate" should read -- tri-n-butyltin maleate --

Signed and Sealed this

Sixth Day of August, 2002

Attest:

JAMES E. ROGAN
*Attesting Officer*     *Director of the United States Patent and Trademark Office*